(12) United States Patent
Meilander et al.

(10) Patent No.: US 8,497,405 B1
(45) Date of Patent: Jul. 30, 2013

(54) PROCESS FOR DISPERSING VAPOROUS HYDROGEN PEROXIDE

(71) Applicants: Timothy W. Meilander, Broadview Hts., OH (US); Paul A. Wiget, Mentor, OH (US); Iain F. McVey, Lakewood, OH (US); Michael A. Centanni, Parma, OH (US)

(72) Inventors: Timothy W. Meilander, Broadview Hts., OH (US); Paul A. Wiget, Mentor, OH (US); Iain F. McVey, Lakewood, OH (US); Michael A. Centanni, Parma, OH (US)

(73) Assignee: STERIS Inc., Temecula, CA (US)

( * ) Notice: Subject to any disclaimer, the term of this patent is extended or adjusted under 35 U.S.C. 154(b) by 0 days.

(21) Appl. No.: 13/780,224

(22) Filed: Feb. 28, 2013

Related U.S. Application Data

(62) Division of application No. 12/033,905, filed on Feb. 20, 2008, now Pat. No. 8,460,605.

(60) Provisional application No. 60/893,134, filed on Mar. 6, 2007, provisional application No. 60/962,876, filed on Aug. 1, 2007.

(51) Int. Cl.
*A62D 3/36* (2007.01)
(52) U.S. Cl.
USPC ............................ 588/318; 588/405; 588/410
(58) Field of Classification Search
USPC ......................... 588/313, 318, 405, 410, 900
See application file for complete search history.

(56) References Cited

U.S. PATENT DOCUMENTS

| | | | |
|---|---|---|---|
| 3,596,602 | A | 8/1971 | Gey |
| 3,661,083 | A | 5/1972 | Weimholt |
| 3,713,383 | A | 1/1973 | Crescenzo et al. |
| 3,831,520 | A | 8/1974 | Bowen et al. |
| 3,898,932 | A | 8/1975 | Flatau et al. |
| 4,170,875 | A | 10/1979 | Edwards |
| 5,037,623 | A | 8/1991 | Schneider et al. |
| 6,213,024 | B1 | 4/2001 | Jasper, Jr. et al. |
| 6,382,105 | B1 | 5/2002 | Jones |
| 6,523,478 | B1 | 2/2003 | Gonzalez |
| 6,532,741 | B2 | 3/2003 | Watkins |
| 6,652,248 | B2 | 11/2003 | Watkins et al. |
| 6,834,494 | B2 | 12/2004 | Lohner et al. |
| 6,887,821 | B2 | 5/2005 | Mays et al. |
| 6,945,175 | B1 | 9/2005 | Gotzmer et al. |
| 7,145,052 | B1 | 12/2006 | Watkins |
| 8,216,523 | B2 | 7/2012 | Meilander et al. |
| 2003/0051462 | A1 | 3/2003 | Watkins |
| 2005/0183615 | A1 | 8/2005 | Flatau |

*Primary Examiner* — Edward Johnson
(74) *Attorney, Agent, or Firm* — Renner, Otto, Boisselle & Sklar, LLP

(57) ABSTRACT

The disclosed invention relates to a decontaminant dispenser which may be used as a projectile. The invention also relates to a decontamination process using the decontaminant dispenser. The decontaminant dispenser may be thrown by hand, launched as an artillery shell or the payload for a missile, or dropped by an airplane into the area to be decontaminated. The dispenser may be placed in the area to be decontaminated. The decontaminant dispenser may be ruggedized for use in hostile environments such as those that may be anticipated for military applications.

20 Claims, 2 Drawing Sheets

PROCESS FOR DISPERSING VAPOROUS HYDROGEN PEROXIDE

This application is a divisional of U.S. patent application Ser. No. 12/033,905 filed on Feb. 20, 2008, which claims the benefit under 35 U.S.C. §119(e) to U.S. Provisional Application No. 60/893,134 filed on Mar. 6, 2007 and U.S. Provisional Application No. 60/962,876 filed on Aug. 1, 2007. These applications are incorporated herein by reference in their entireties.

TECHNICAL FIELD

This invention relates to a decontaminant dispenser which is suitable for use as a projectile.

BACKGROUND

Decontaminant generating systems, such as those used to generate vaporous hydrogen peroxide (VHP), have been used to decontaminate large enclosures such as rooms and buildings (e.g., hotel rooms, hospital wards, scientific laboratories, etc.) from contaminants such as bacteria, molds, fungi, yeasts, and the like.

SUMMARY

It would be advantageous for the military to use these decontaminant systems in the field for defense against chemical and biological weapons. However, there are situations in the field where, due to the terrain or remoteness of the location, it is not possible to transport these systems to the field location. This invention provides a solution to this problem. The inventive decontaminant dispenser is suitable for use as a projectile and, as such, may be thrown by a person, launched as a projectile (e.g., artillery shell or the payload for a missile), or dropped by an airplane to deliver the dispenser to a location where it is desired to dispense a decontaminant and thereby conduct a decontamination. The inventive decontaminant dispenser may be carried by hand and placed in an area to be decontaminated. The inventive decontaminant dispenser may be used to decontaminate contaminated objects on the ground or to neutralize a contaminated air space such as a toxic cloud resulting from the detonation of a chemical and/or biological warfare agent device. The decontaminant dispenser may be used in a large enclosure such as the room of a building by throwing, launching or dropping the dispenser into the enclosure, or by placing the dispenser in the enclosure. The inventive decontaminant dispenser employs VHP, or VHP in combination with ammonia as the decontaminant. The dispenser employs catalytic discharge to vaporize and discharge the decontaminant.

This invention relates to a decontaminant dispenser suitable for use as a projectile, comprising: a container suitable for containing propellant grade liquid hydrogen peroxide, the container comprising a container wall with at least one opening in the container wall and a pressure release membrane positioned in the opening, the pressure release membrane being adapted to rupture when pressure within the container exceeds a predetermined value; and at least one catalytic probe adapted to be inserted into the container in contact with the liquid hydrogen peroxide, the catalytic probe being undersized so that when inserted into the container in contact with the hydrogen peroxide part of the hydrogen peroxide in the container reacts in an exothermic reaction to form a product composition, the product composition comprising water, oxygen, and unreacted hydrogen peroxide, the reaction being sufficient to generate an expansion of the product composition, the expansion being sufficient to rupture the pressure release membrane and drive the unreacted hydrogen peroxide through the at least one opening.

This invention relates to a process for dispensing vaporous hydrogen peroxide using the foregoing dispenser, the process comprising: filling the container with propellant grade hydrogen peroxide; and inserting the catalytic probe into the container in contact with the hydrogen peroxide to initiate an exothermic reaction resulting in the formation of a product composition comprising water, oxygen and unreacted hydrogen peroxide, the reaction expanding the product composition sufficiently to rupture the pressure release membrane and drive unreacted hydrogen peroxide through the opening in the container wall.

With the foregoing dispenser, the container may comprise an inner chamber and an outer chamber, the inner chamber being positioned within the outer chamber; the inner chamber being suitable for containing propellant grade liquid hydrogen peroxide, the inner chamber comprising an inner chamber wall with at least one inner opening in the inner chamber wall and an inner pressure release membrane positioned in the inner opening, the inner pressure release membrane being adapted to rupture when the pressure within the inner chamber exceeds a predetermined value; the outer chamber being suitable for containing gaseous ammonia, the outer chamber comprising an outer chamber wall with at least one outer opening in the outer chamber wall and an outer pressure release membrane positioned in the outer opening, the outer pressure release membrane being adapted to rupture when the pressure within the outer chamber exceeds a predetermined value; the catalytic probe being adapted to be inserted through the outer chamber into the inner chamber in contact with the liquid hydrogen peroxide.

This invention also relates to a process for dispensing vaporous hydrogen peroxide and gaseous ammonia using the foregoing dispenser, the process comprising: filling the inner chamber with propellant grade hydrogen peroxide; filling the outer chamber with gaseous ammonia; and inserting the catalytic probe through the outer chamber into the inner chamber in contact with the hydrogen peroxide to initiate an exothermic reaction resulting in the formation of a product composition comprising water, oxygen and unreacted hydrogen peroxide, the reaction expanding the product composition sufficiently to rupture the inner pressure release member and the outer pressure release member and drive unreacted hydrogen peroxide through the inner opening in the inner chamber wall and through the outer opening in the outer chamber wall and drive the gaseous ammonia through the outer opening in the outer chamber wall.

BRIEF DESCRIPTION OF THE DRAWINGS

In the annexed drawings all parts and features have like references. A number of the annexed drawings are schematic illustrations which are not necessarily proportioned accurately or drawn to scale.

DETAILED DESCRIPTION

All ranges and ratio limits disclosed in the specification and claims may be combined in any manner. It is to be understood that unless specifically stated otherwise, references to "a", "an", and/or "the" may include one or more than one, and that reference to an item in the singular may also include the item in the plural. All combinations specified in the claims may be combined in any manner.

The term "projectile" is used herein to refer to an object which may be thrown by a person, launched as a projectile (e.g., an artillery shell or the payload for a missile), or dropped by an airplane.

The term "ruggedized," and like terms such as "ruggedization," are used herein to refer to apparatus that is: (1) hardened to ensure that five exposures to chemical, biological, radiological or nuclear (CBRN) contaminants, decontaminants and decontaminating procedures over a thirty-day period do not cause the apparatus to require corrective maintenance during that thirty-day period; (2) capable of being used at temperatures ranging from about −32° C. to about 49° C.; (3) capable of being used in relative humidities ranging from about 5% to about 100%; and/or (4) capable of operating when exposed to conventional hazards of solar radiation, rain, fungus, salt fog, sand, dust, vibration and/or shock in accordance with Military Standard 810 (MIL-STD-810).

Figure 1:
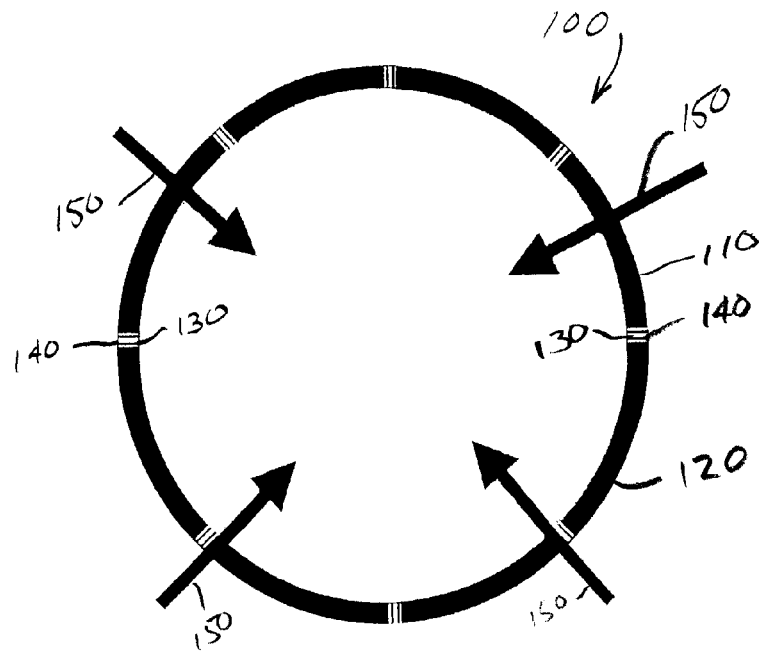
FIG. 1 is a schematic illustration of one embodiment of the inventive decontaminant dispenser.
Figure 3:
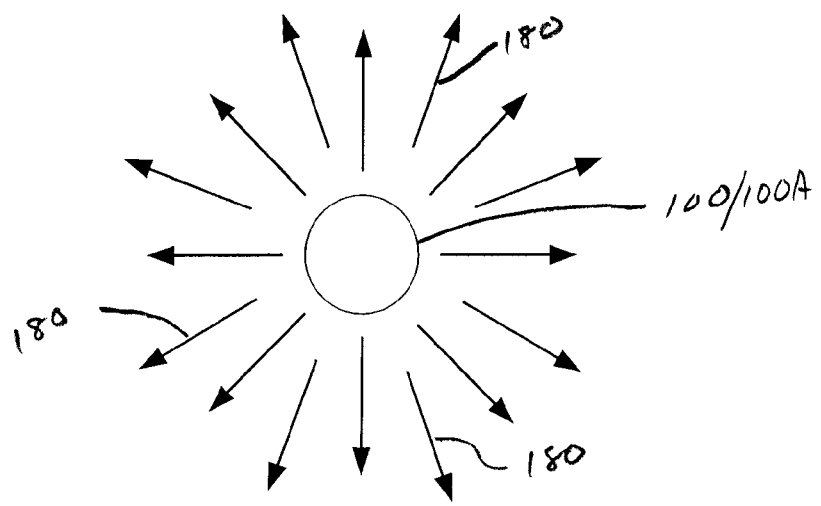
FIG. 3 is a schematic illustration of the decontaminant dispenser of FIG. 1 or FIG. 2 dispensing decontaminant.

The inventive decontaminant dispenser, in its illustrated embodiments, will be described initially with reference to FIG. 1. Referring to FIG. 1, the decontaminant dispenser 100 is suitable for dispensing or dispersing VHP as the decontaminant. The decontaminant dispenser 100 may comprise container 110 which is suitable for containing propellant grade liquid hydrogen peroxide. The container 110 comprises container wall 120 which has at least one opening 130, and in one embodiment a plurality of openings 130, in the container wall 120. A pressure release membrane 140 is positioned in the one or more openings 130. The pressure release membrane 140 is adapted to rupture when pressure within the container 110 exceeds a predetermined value. One or more catalytic probes 150 are adapted to be inserted into the container 110 in contact with the liquid hydrogen peroxide in the container. The catalytic probes 150 may be undersized so that when inserted into the container 110 in contact with the hydrogen peroxide, part but not all of the hydrogen peroxide in the container reacts in an exothermic reaction to form a product composition, the product composition comprising water, oxygen, and unreacted hydrogen peroxide. The reaction may be sufficient to generate an expansion of the product composition sufficient to rupture the pressure release membrane 130 and drive the unreacted hydrogen peroxide through the one or more openings 130. This may result in the spraying of entrained unreacted hydrogen peroxide from the dispenser 100 as illustrated in FIG. 3. Referring to FIG. 3, one or more streams 180 of hydrogen peroxide may be discharged by the dispenser 100.

Figure 2:
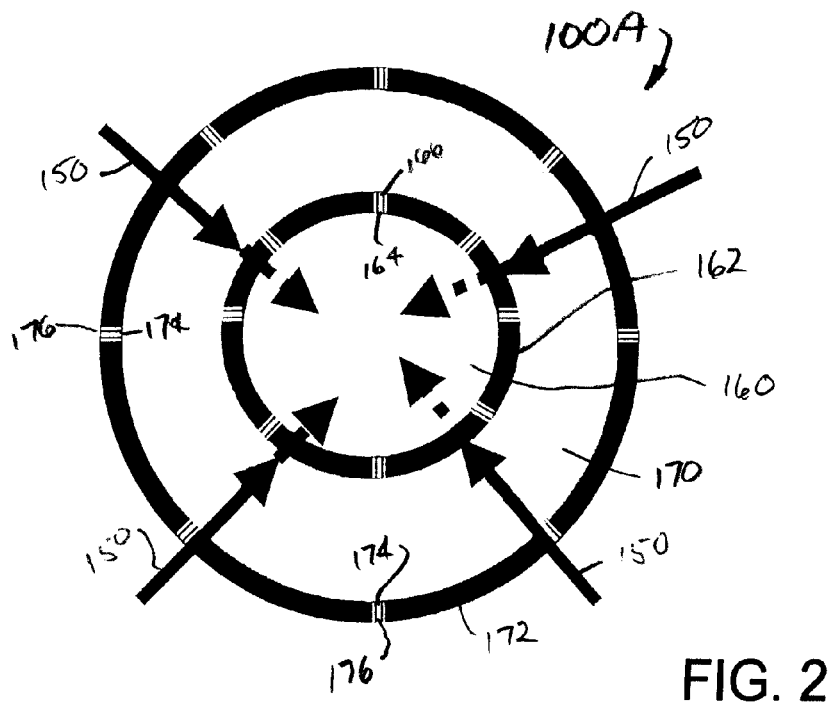
FIG. 2 is a schematic illustration of a modified embodiment of the inventive decontaminant dispenser.

When it is desired to use ammonia in combination with VHP as the decontaminant, the dispenser 100 may be modified as illustrated in FIG. 2. Referring to FIG. 2, the modified dispenser, which is identified in FIG. 2 as decontaminant dispenser 100A, comprises inner chamber 160 and an outer chamber 170. The inner chamber 160 is positioned within the outer chamber 170. The inner chamber 160 is suitable for containing propellant grade liquid hydrogen peroxide. The inner chamber 160 comprises inner chamber wall 162 which has at least one inner opening 164 in the inner chamber wall 162. In one embodiment, a plurality of the inner openings 164 are in the inner chamber wall 162. An inner pressure release membrane 166 is positioned in the one or more inner openings 164. The inner pressure release membrane 166 is adapted to rupture when the pressure within the inner chamber 160 exceeds a predetermined value. The outer chamber 170 is suitable for containing gaseous ammonia. The outer chamber 170 comprises outer chamber wall 172 which includes at least one outer opening 174, and in one embodiment a plurality of outer openings 174. An outer pressure release membrane 176 is positioned in the one or more outer openings 174. The outer pressure release membrane 176 is adapted to rupture when the pressure within the outer chamber 170 exceeds a predetermined value. One or more catalytic probes 150 are adapted to be inserted through the outer chamber 170 into the inner chamber 160 in contact with the liquid hydrogen peroxide. The catalytic probes 150 may be undersized so that when inserted through the outer chamber 170 into the inner chamber 160 in contact with the hydrogen peroxide, part but not all of the hydrogen peroxide in the chamber 160 reacts in an exothermic reaction to form a product composition, the product composition comprising water, oxygen, and unreacted hydrogen peroxide. The reaction may be sufficient to generate an expansion of the product composition sufficient to rupture the pressure release membranes 166 and 176 and drive the unreacted hydrogen peroxide through the one or more inner openings 164 and outer openings 174. The ammonia gas in the outer chamber 170 may be drawn through the outer chamber openings with the unreacted hydrogen peroxide. This may result in the spraying of entrained unreacted hydrogen peroxide and ammonia gas from the dispenser 100A as illustrated in FIG. 3. Referring to FIG. 3, one or more streams 180 of hydrogen peroxide and ammonia gas may be discharged by the dispenser 100A.

Figure 4:
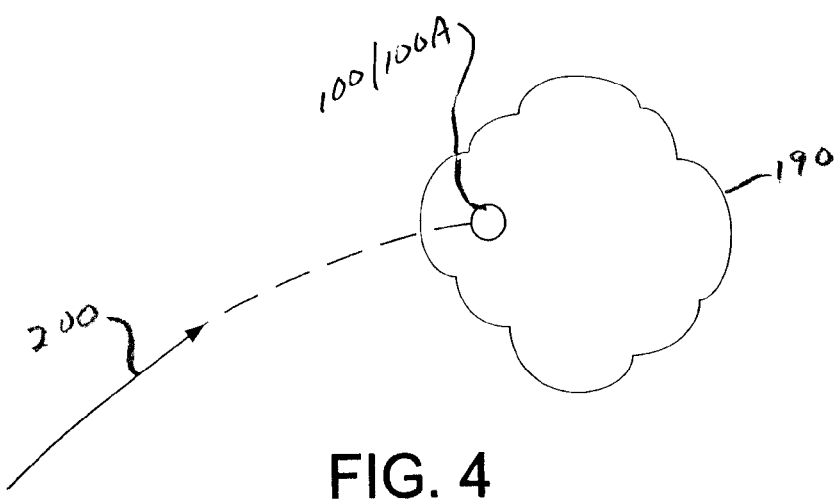
FIG. 4 is a schematic illustration showing the launch of the decontaminant dispenser of FIG. 1 or FIG. 2 as a projectile into a toxic cloud.

The decontaminant dispensers 100 and 100A may have any desired shape to provide the desired suitability as a projectile. The dispensers 100 and 100A may have a cylindrical shape or a spherical shape. These dispensers may be in the form of an artillery shell or a hand grenade. The decontaminant dispenser 100 or 100A may be thrown by a person, launched as a projectile (e.g., artillery shell or the payload for a missile), or dropped by an airplane to deliver the dispenser to a location where it is desired to dispense a decontaminant and thereby conduct a decontamination. The inventive decontaminant dispenser may be carried by hand and placed in an area to be decontaminated. The inventive decontaminant dispenser may be used to decontaminate contaminated objects on the ground. The decontaminant dispenser 100 or 100A may be thrown, launched or dropped into a contaminated air space such as a toxic cloud resulting from the detonation of a chemical and/or biological warfare agent device. The decontaminant may used to neutralize the toxic cloud or destroy the contaminants in the toxic cloud. This is illustrated in FIG. 4 where the decontaminant dispenser 100 or 100A is launched along projectile path 200 into toxic cloud 200. The decontaminant dispenser may be used in a large enclosure such as the room of a building by throwing, launching or dropping the dispenser into the enclosure, or by placing the dispenser in the enclosure.

The container wall 120, as well as the chamber walls 162 and 172, may be made of any material that is sufficient to provide the desired properties of strength and lightweight, as well as resistance to harmful materials and conditions likely to be encountered. The walls 120, 162 and 172 may be ruggedized. The walls 120, 162 and 172 may be made of a metal alloy that does not react with hydrogen peroxide. The walls 120, 162 and 172 may be made of stainless steel, coated steel, aluminum, an aluminum alloy, anodized aluminum, and the like.

The container 110 and the inner chamber 160 may each have an internal volume in the range from about 100 cubic centimeters to about 500 liters, and in one embodiment from in the range from about 200 cubic centimeters to about 200 liters. The outer chamber 170 may have an internal volume (that is, the volume of the annular space between the outer chamber wall 172 and the inner chamber wall 162) in the range from about 200 cubic centimeters to about 1500 liters, and in one embodiment in the range from about 500 cubic centimeters to about 500 liters. The ratio of the internal volume of the outer chamber 170 to the internal volume of the inner chamber 160 may be in the range from about 1:1 to about 4:1, and in one embodiment in the range from about 2:1 to about 3:1.

The weight of the decontaminant dispenser 100 when fully loaded with hydrogen peroxide, and the weight of the dispenser 100A when fully loaded with hydrogen peroxide and ammonia, may be in the range from about 0.1 to about 500 Kg, and in one embodiment in the range from about 0.5 to about 100 Kg.

The number of openings 130 in the container wall 120 and the number of inner openings 164 in the inner chamber wall 162 may be in the range from 1 to about 100, and in one embodiment in the range from about 1 to about 20. The number of outer openings 174 in the outer chamber wall 172 may be in the range from 1 to about 100, and in one embodiment in the range from about 1 to about 20. The average diameter of the openings 130, 164 and 174 may be in the range from about 0.1 to about 10 millimeters (mm), and in one embodiment in the range from about 0.1 to about 2 mm.

The pressure release membranes 140, 166 and 176 may be made of any suitable material that ruptures at the desired pressure. The pressure release membranes may be made of a material comprising aluminized polyolefin, polyester, polytetrafluoroethylene, spun polyethylene, and the like. The pressure release membranes may be adapted to rupture when the pressure within the container 110 or the inner chamber 160 resulting from the exothermic reaction of the hydrogen peroxide and the resulting expansion of the product composition exceeds a predetermined value. This predetermined value may be in the range from about 2 to about 35 atmospheres, and in one embodiment from about 3 to about 15 atmospheres. When the pressure release membrane 140, or the pressure release membranes 166 and 176, rupture, the product composition formed by the exothermic reaction of the hydrogen peroxide may discharge from the container 110 through the openings 130, or from the inner chamber 160 through the openings 164 in the inner chamber wall 162 and through the openings 174 in the outer chamber wall 172.

The propellant grade hydrogen peroxide used with the decontaminant dispenser 100 or 100A may have a relatively high concentration of hydrogen peroxide. The hydrogen peroxide concentration may be about 70% by weight or higher, and in one embodiment in the range from about 70% to about 98% by weight, and in one embodiment from about 80% to about 98%, and in one embodiment from about 85% to about 98% by weight, and in one embodiment from about 90% to about 98% by weight, and in one embodiment from about 95% to about 98% by weight, and in one embodiment the concentration may be about 98% by weight.

The one or more catalytic probes 150 may employ any catalyst suitable for decomposing hydrogen peroxide. The catalytic probe 150 may comprise a deposit, plating or coating formed on a catalyst insert rod. The catalyst may comprise one or more suitable transition metals, transition metal oxides, or combination thereof. The catalyst may comprise Ag, Mn, Pd, Pt, Rh, an oxide of one or more of the foregoing metals, or a mixture of two or more of the foregoing metals and/or oxides. The catalyst may be supported by a suitable support such as an alumina support. The catalyst may comprise a silver based alloy. The catalyst may comprise manganese dioxide. Any desired number of catalytic probes 150 may be used with the dispenser 100 or 100A. For example, from 1 to about 10 catalytic probes 150 may be used, and in one embodiment from 1 to about 4 or about 5 catalytic probes 150 may be used. The catalyst may be relatively undersized so as to not decompose all of the hydrogen peroxide in the container 110 or the inner chamber 160. The amount of hydrogen peroxide reacting in the container 110 or the inner chamber 160 to form water and oxygen may be from about 50 to about 75 percent by weight of the hydrogen peroxide in the container 110 or the inner chamber 160 prior to commencing the catalytic reaction, and in one embodiment in the range from about 60 to about 70 percent by weight.

The temperature of the contents of the dispenser 100 or 100A prior to rupture of the pressure release membrane 140, or 166 and 176, may be in the range from about 120 to about 400° C., and in one embodiment in the range from about 200 to about 300° C. The pressure in the dispenser 100 or 100A prior to the rupture of the pressure release membranes 140, or 166 and 176, may build to a level in the range from about 2 to about 35 atmospheres, and in one embodiment in the range from about 3 to about 15 atmospheres. The time required for the reaction to generate sufficient pressure to rupture the pressure release membranes 140, or 166 and 176, may be in the range from about 2 to about 60 seconds, and in one embodiment in the range from about 5 to about 30 seconds. The flow rate of the contents of the dispenser 100 or 100A through the openings 130 or 174 may be in the range from about 0.01 to about 10 kilograms per second (Kg/s), and in one embodiment in the range from about 0.5 to about 5 Kg/s.

The decontaminant dispensers 100 and 100A may be used in hostile environments such as those that may be anticipated for military applications. The dispensers 100 and 100A may be ruggedized. When intended for use in such hostile environments, the decontaminant dispensers 100 and 100A may be constructed using any material that is sufficient to provide the required properties of strength and lightweight, as well as ruggedization. Ruggedization may include providing resistance to hot and cold temperatures, solar radiation, rain, fungus, salt fog, sand and/or dust, resistance to vibration and shock, as well as resistance to CBRN contaminants. This may involve construction of the decontaminant dispensers 100 and 100A in compliance with military standard MIL-STD-810.

The decontaminant produced by the decontaminant dispenser 100 comprises VHP, and the decontaminant produced by the dispenser 100A comprises VHP and gaseous ammonia. The addition of ammonia may be used to control the pH of the decontaminant. When the decontaminant contacts contaminated objects to be decontaminated, the process may be regarded as a dry process characterized by the absence of condensate formation on the surfaces of the contaminated objects being decontaminated. Alternatively, the process may be regarded as a wet process characterized by the formation of a condensate in the form of a liquid film on the surfaces of the contaminated objects. The liquid film may have a film layer thickness in the range up to about 20 microns, and in one embodiment up to about 10 microns, and in one embodiment up to about 5 microns, and in one embodiment up to about 1 micron. The film layer may be referred to as a microcondensate layer of hydrogen peroxide.

VHP, when used in combination with ammonia gas, may be referred to as modified VHP or mVHP. The volumetric ratio of VHP to ammonia gas may be in the range from about 1:1 to about 1:0.0001. VHP and mVHP may be effective microbial and chemical decontaminants because they may provide a broad spectrum of activity against a wide variety of pathogenic microorganisms and chemical pathogenic agents, such as hard to destroy spores of *Bacillus stearothermophilus*, *Bacillus anthracis*, smallpox virus, and the like. They may be also effective at or close to room temperature (e.g., about 15 to about 30° C.). VHP and mVHP may have good material compatibility, rendering them safe for use with a variety of equipment and materials, including electronic equipment, and the like. VHP may degrade to water and oxygen over time.

The contaminated objects that may be decontaminated using the dispensers 100 or 100A may be contaminated with any contaminant. The objects to be decontaminated may include any object exposed to the contaminant including military weapons, clothing, body armor, as well as sensitive equipment such as computers, test equipment, optical devices, electronic devices, communications equipment, and the like. These may include radio headsets and night vision goggles, as well as other small but high value pieces of equipment. The contaminant may comprise one or more chemical, biological, radiological and/or nuclear (CBRN) warfare agents.

Different levels of decontamination may be accomplished. As used herein, the term "decontamination," may encompass both microbial decontamination as well as chemical decontamination--the destruction of chemical agents, or their conversion to harmless or odorless compounds. Decontamination may also encompass the neutralizing of unpleasant odors, such as odors and dampness due to molds. "Microbial decontamination" may be used herein to encompass the destruction of biological contaminants, specifically, living microorganisms, and also the destruction or inactivation of pathogenic forms of proteinaceous-infectious agents (prions). The term microbial decontamination may encompass sterilization, the highest level of biological contamination control, which connotes the destruction of all living microorganisms. The term may also include disinfection, the destruction of harmful microorganisms, and sanitizing, which connotes being free from germs. "Chemical decontamination" is intended to encompass the destruction of pathogenic chemical agents or their conversion to less harmful or odiferous species.

Exemplary biological contaminants which may be destroyed using the decontaminant dispenser 100 or 100A may include bacterial spores, vegetative bacteria, viruses, molds, and fungi. Some of these may be capable of killing or causing severe injury to mammals, particularly humans. Included among these are viruses, such as equine encephalomyelitis and smallpox, the coronavirus responsible for Severe Acute Respiratory Syndrome (SARS); bacteria, such as those which cause plague (*Yersina pestis*), anthrax (*Bacillus anthracis*), and tularemia (*Francisella tularensis*); and fungi, such as coccidioidomycosis; as well as toxic products expressed by such microorganisms; for example, the botulism toxin expressed by the common *Clostridium botulinium* bacterium.

Also included are the less harmful microorganisms, such as those responsible for the common cold (rhinoviruses), influenza (orthomyxoviruses), skin abscesses, toxic shock syndrome (*Staphylococcus aureus*), bacterial pneumonia (*Streptococcus pneumoniae*), stomach upsets (*Escherichia coli, Salmonella*), and the like.

Exemplary pathogenic chemical agents may include substances which are often referred to as chemical warfare agents, such as poison gases and liquids, particularly those which are volatile, such as nerve gases, blistering agents (also known as vesicants), and other extremely harmful or toxic chemicals. As used herein, the term "chemical pathogenic agent" is intended to include only those agents which are effective in relatively small dosages to substantially disable or kill mammals and which can be degraded or otherwise rendered harmless by a process which includes oxidation.

Exemplary chemical pathogenic agents may include choking agents, such as phosgene; blood agents, which act on the enzyme cytochrome oxidase, such as cyanogen chloride and hydrogen cyanide; incapacitating agents, such as 3-quinuclidinyl benzilate ("BZ"), which blocks the action of acetylcholine; vesicants, such as di(2-chloroethyl) sulfide (mustard gas or "HD") and dichloro(2-chlorovinyl)arsine (Lewisite); nerve agents, such as ethyl-N,N dimethyl phosphoramino cyanidate (Tabun or agent GA), o-ethyl-S-(2-diisopropyl aminoethyl) methyl phosphono-thiolate (agent VX), isopropyl methyl phosphonofluoridate (Sarin or Agent GB), methylphosphonofluoridic acid 1,2,2-trimethylpropyl ester (Soman or Agent GD).

While the disclosed invention has been explained in relation to various detailed embodiments, it is to be understood that various modifications thereof may become apparent to those skilled in the art upon reading the specification. Therefore, it is to be understood that the invention specified herein is intended to include such modifications as may fall within the scope of the appended claims.

The invention claimed is:

1. A process for dispersing vaporous hydrogen peroxide using a decontaminant dispenser suitable for use as a projectile, wherein the dispenser comprises a container suitable for containing propellant grade liquid hydrogen peroxide, the container comprising a container wall with at least one opening in the container wall and a pressure release membrane positioned in the opening, the pressure release membrane being adapted to rupture when pressure within the container exceeds a predetermined value; and at least one catalytic probe adapted to be inserted into the container in contact with the liquid hydrogen peroxide, the catalytic probe being undersized so that when inserted into the container in contact with the hydrogen peroxide part of the hydrogen peroxide in the container reacts in an exothermic reaction to form a product composition, the product composition comprising water, oxygen, and unreacted hydrogen peroxide, the reaction being sufficient to generate an expansion of the product composition, the expansion being sufficient to rupture the pressure release membrane and drive the unreacted hydrogen peroxide through the at least one opening, the process comprising:

filling the container with propellant grade hydrogen peroxide; and inserting the catalytic probe into the container in contact with the hydrogen peroxide to initiate an exothermic reaction resulting in the formation of a product composition comprising water, oxygen and unreacted hydrogen peroxide, the reaction expanding the product composition sufficiently to rupture the pressure release membrane and drive unreacted hydrogen peroxide through the opening in the container wall.

2. A process for dispersing vaporous hydrogen peroxide and gaseous ammonia using a decontaminant dispenser suitable for use as a projectile, wherein the dispenser comprises a container suitable for containing propellant grade liquid hydrogen peroxide, the container comprising a container wall with at least one opening in the container wall and a pressure release membrane positioned in the opening, the pressure release membrane being adapted to rupture when pressure within the container exceeds a predetermined value; and at least one catalytic probe adapted to be inserted into the container in contact with the liquid hydrogen peroxide, the catalytic probe being undersized so that when inserted into the container in contact with the hydrogen peroxide part of the hydrogen peroxide in the container reacts in an exothermic reaction to form a product composition, the product composition comprising water, oxygen, and unreacted hydrogen peroxide, the reaction being sufficient to generate an expansion of the product composition, the expansion being sufficient to rupture the pressure release membrane and drive the unreacted hydrogen peroxide through the at least one opening, wherein the container comprises an inner chamber and an outer chamber, the inner chamber being positioned within the outer chamber; the inner chamber being suitable for containing propellant grade liquid hydrogen peroxide, the inner chamber comprising an inner chamber wall with at least one inner opening in the inner chamber wall and an inner pressure release membrane positioned in the inner opening, the inner pressure release membrane being adapted to rupture when the pressure within the inner chamber exceeds a predetermined value; the outer chamber being suitable for containing gaseous ammonia, the outer chamber comprising an outer chamber wall with at least one outer opening in the outer chamber wall and an outer pressure release membrane positioned in the outer opening, the outer pressure release membrane being adapted to rupture when the pressure within the outer chamber exceeds a predetermined value; and the catalytic probe being adapted to be inserted through the outer chamber into the inner chamber in contact with the liquid hydrogen peroxide, the process comprising:

filling the inner chamber with propellant grade hydrogen peroxide;

filling the outer chamber with gaseous ammonia; and inserting the catalytic probe through the outer chamber into the inner chamber in contact with the hydrogen peroxide to initiate an exothermic reaction resulting in the formation of a product composition comprising water, oxygen and unreacted hydrogen peroxide, the reaction expanding the product composition sufficiently to rupture the inner pressure release member and the outer pressure release member and drive unreacted hydrogen peroxide through the inner opening in the inner chamber wall and through the outer opening in the outer chamber wall and drive the gaseous ammonia through the outer opening in the outer chamber wall.

3. The process of claim 1 wherein from about 50 to about 75 percent by weight of the hydrogen peroxide is converted to water and oxygen in the container.

4. The process of claim 2 wherein the mole ratio of hydrogen peroxide in the inner chamber to gaseous ammonia in the outer chamber is in the range from about 1:1 to about 1:0.0001.

5. The process of claim 1 wherein the exothermic reaction in the container is sufficient to heat the contents of the container to a temperature in the range from about 120 to about 400° C.

6. The process of claim 1 wherein the exothermic reaction in the container is sufficient to increase the pressure in the container to a pressure in the range from about 2 to about 35 atmospheres prior to rupturing the pressure release membrane.

7. The process of claim 1 wherein the dispenser is thrown by a person after inserting the catalytic probe into the container.

8. The process of claim 1 wherein the dispenser is launched as a projectile after inserting the catalytic probe into the container.

9. The process of claim 1 wherein the dispenser is dropped from an airplane after inserting the catalytic probe into the container.

10. The process of claim 1 wherein the dispenser is placed in an enclosure after inserting the catalytic probe.

11. The process of claim 1 wherein the dispenser is thrown, launched or dropped into a toxic cloud comprising a chemical and/or biological warfare agent after inserting the catalytic probe into the container.

12. The process of claim 1 wherein the unreacted hydrogen peroxide driven through the opening in the container wall contacts contaminated objects to be decontaminated.

13. The process of claim 12 wherein the contaminated objects comprise one or more of military weapons, clothing, body armor, radio headsets, night vision goggles, computers, test equipment, optical devices, electronic devices and/or communications equipment.

14. The process of claim 12 wherein the contaminated objects are contaminated with one or more chemical, biological, radiological and/or nuclear warfare agents.

15. The process of claim 12 wherein the contaminated objects are contaminated with one or more bacterial spores, vegetative bacteria, viruses, molds and/or fungi.

16. The process of claim 12 wherein the contaminated objects are contaminated with one or more pathogenic chemical agents.

17. The process of claim 12 wherein the step of contacting the contaminated objects with the unreacted hydrogen peroxide comprises a dry process characterized by the absence of condensate formation on the surface of the contaminated objects being decontaminated.

18. The process of claim 12 wherein the step of contacting the contaminated objects with the unreacted hydrogen peroxide comprises a wet process characterized by the formation of condensate in the form of a liquid film on the surface of the contaminated objects being decontaminated.

19. The process of claim 18 wherein the condensate comprises hydrogen peroxide.

20. The process of claim 1 wherein the decontaminant dispenser is ruggedized.

* * * * *